United States Patent
Glucina et al.

(10) Patent No.: US 6,370,943 B1
(45) Date of Patent: Apr. 16, 2002

(54) PROCESS FOR MONITORING THE INTEGRITY OF HOLLOW FIBER FILTRATION MODULES

(75) Inventors: K. Glucina, St Germain en Laye; J. M. Laine, Ecquevilly; P. Moulart, Rueil Malmaison; M. R. Chevalier, Bougival, all of (FR)

(73) Assignee: Suez-Lyonnaise des Eaux, Nanterre (FR)

( * ) Notice: Subject to any disclaimer, the term of this patent is extended or adjusted under 35 U.S.C. 154(b) by 0 days.

(21) Appl. No.: 09/623,371
(22) PCT Filed: Feb. 22, 1999
(86) PCT No.: PCT/FR99/00393
§ 371 Date: Sep. 1, 2000
§ 102(e) Date: Sep. 1, 2000
(87) PCT Pub. No.: WO99/44728
PCT Pub. Date: Sep. 10, 1999

(30) Foreign Application Priority Data

Mar. 2, 1998 (FR) ............................................ 98 02491

(51) Int. Cl.⁷ .................................................. G01N 15/08
(52) U.S. Cl. ......................................... 73/38; 73/40.5 A
(58) Field of Search .............................. 73/38, 40.5 A, 73/863.23; 210/87

(56) References Cited

U.S. PATENT DOCUMENTS

| | | | |
|---|---|---|---|
| 3,693,406 A | * | 9/1972 | Tobin, III ...................... 73/38 |
| 4,609,994 A | * | 9/1986 | Bassim et al. ............ 73/40.5 A |
| 4,744,240 A | * | 5/1988 | Reichelt ......................... 73/38 |
| 5,602,327 A | * | 2/1997 | Torizuka et al. .......... 73/40.5 A |

FOREIGN PATENT DOCUMENTS

| EP | 0640822 A2 | * | 3/1995 | |
| JP | 60063438 A | * | 4/1985 | .............. 73/40.5 A |

OTHER PUBLICATIONS

WO 94/09890 to Drummond et al., published May 1994.*

WO/94/11721 to Hopkins et al., published May 1994.*

* cited by examiner

Primary Examiner—Hezron Williams
Assistant Examiner—Michael Cygan
(74) Attorney, Agent, or Firm—Connolly Bove Lodge & Hutz LLP

(57) ABSTRACT

A process is disclosed for monitoring the integrity of hollow fiber filtration modules and for detecting leaks of treated liquid through a fiber completely or partially broken. It operates continuously and in filtration mode, without production shutdown. The process includes detecting the noise caused by the passage of the liquid through a ruptured fiber. The noise signal thus obtained is amplified. The amplified signal thus obtained is compared with a threshold noise level, within the same range of frequencies, which is characteristic of intact modules, this comparison making it possible to detect whether or not the module is intact.

2 Claims, 1 Drawing Sheet

PROCESS FOR MONITORING THE INTEGRITY OF HOLLOW FIBER FILTRATION MODULES

FIELD OF THE INVENTION

The present invention relates to a process and to a device intended to monitor the integrity of microfiltration or ultrafiltration modules which are used in procedures for separating and concentrating solutions and especially in the field of water treatment.

BACKGROUND OF THE INVENTION

It is known that such modules use a number of hollow fibres grouped together in bundles and the problem for which the present invention proposes a solution is that of detecting a fibre rupture which leads to fluid passing directly from the dirty side of the membrane (concentrate) to the clean side (permeate) through the fibre or fibres which are completely or partially broken.

To date there are a number of processes for detecting the modification of the integrity of micro- or ultrafiltration modules which can be placed into two categories:

processes monitoring treated water quality, processes detecting leaks using a physical procedure.

A few details will be given below concerning the state of the prior art corresponding to processes belonging to the two categories above:

Monitoring Treated Water Quality

Measurement of Turbidity

Water treated through a membrane generally has a turbidity of lower than 0.1 NTU (nephelometric turbidity unit). A failure in the module integrity should therefore be translated into an increase in turbidity. However if the water to be treated is not very turbid, the effect of dilution makes it impossible to detect a leak from one broken fibre out of tens of thousands of fibres, i.e. several modules. Detection will only be effective if the water to be treated is very contaminated. For example, if contaminated water is treated with 0.8 g/l of active carbon in powder form, one broken fibre out of 120,000 (8 modules) is easily detected. With low turbidity raw water, for example 0.5 NTU, the detection of one broken fibre out of 15,000 (a single module) is not assured.

Particle Counting

This process is much more sensitive than that of measuring turbidity but it also has limits. With this technique, it is possible to detect one broken fibre out of 420,000 fibres treating relatively contaminated water (0.15 mg/l of active carbon) and operating in tangential mode. In frontal mode and with low turbidity water, it is possible to detect a broken fibre in only a few modules, i.e. around 100,000 fibres. In addition, this process requires considerable care and maintenance.

Bacteriological Analyses

This is a process which is arduous and lengthy to implement and which is subject to external contamination. At least two consecutive negative results are needed in order to start confirming a leak. This process may use a Colibacillus detector, but it has been noted that, even when not intact, the membranes generally produced water free from *Escherichiae Coli*. This system therefore cannot be applied. Furthermore, detection requires several days.

In conclusion, methods based on monitoring treated water quality are more or less reliable and they have limited accuracy. They are global, given that the measurement is carried out at station level for a group of filtration machines, or at best a single machine comprising several modules. So other methods then need to be applied to find the failed module. The detection process is therefore too lengthy.

Detection of Leaks

Air Pressure Test

This is the most well-known test which consists in trapping a volume of air under pressure on one side of the membrane and in measuring the time required for a given drop of pressure through the membrane. Since the pores of the membrane are filled with water, the air diffuses slowly through this water and the pressure drops slowly at a standard rate. If the drop is faster, this means that the membrane leaks and therefore that at least one fibre is broken. This method is relatively accurate if it is implemented module by module. However, in this case a manual operation is needed to isolate the module and to connect up the air. This method is approximate when it is implemented on the scale of one filtration machine. Furthermore, the ageing of modules causes the speed of air diffusion to vary and it then becomes difficult to distinguish between a broken fibre and a general increase in the porosity of the membrane.

Air Diffusion Test

When implementing this process, one of the sides of the membrane is kept under water and the other is subjected to a low air pressure. If the membrane is not intact, the air passing through the leak causes a rapid increase in the water side pressure. This technique is free from interference due to air diffusion which is much slower in this case, since the water needs to become saturated with dissolved air then it needs degassing before air diffusion occurs.

Acoustic Detection

This technique consists in using a stethoscope to identify a module which leaks when air passes through a broken fibre. The "bubbling" thus produced on the water side is easily audible. This auscultation is carried out by an operator.

WO 94 09890 describes a process for detecting a defective fibre in a filtration system having microfiltration membranes. According to this process, a gas under pressure is delivered into the vessel contained between the fibres of the membrane and the filter envelope and the formation of bubbles, indicating the presence of a defective fibre, is detected at the ends of the fibres. This process therefore makes use of a "bubble point", after isolating the module or the bank of several modules. It therefore involves a biphasic, gas-liquid system which can only be used after the plant is shut down.

WO 94/11729 also relates to a detection method which requires a plant shutdown with the presence of gas on both sides of the membrane.

U.S. Pat. No. -A-4744240 relates to a process for treating microfiltration modules which also makes use of the application of a gas through a membrane and measurement of a bubble point which is representative of the size of the pores or the holes present in the membrane. In this system, which is a biphasic gas-liquid system, the plant also has to be shut down to make the measurement.

In conclusion, the technique for monitoring the integrity of modules based on leak detection is a global technique applied to a set of modules (a filtration machine) and making it possible to detect a leak without the possibility of identifying the failed module. This technique can only be implemented during a production shutdown and it requires a minimum of several minutes. Furthermore, should a failure be noticed, an additional intervention (for example listening by stethoscope) needs to be carried out in order to identify the failed module, this listening also having to be carried out after production shutdown.

BRIEF DESCRIPTION OF THE INVENTION

The present invention intends to provide a process which does not have the drawbacks of the solutions mentioned above.

The subject of the invention is therefore a process for monitoring the integrity of hollow fibre filtration modules and for detecting leaks of treated liquid through a fibre completely or partially broken, characterized in that it consists, continuously and in filtration mode, without production shutdown, in:

detecting the noise caused by the passage of the liquid through a ruptured fibre;

amplifying the noise signal thus obtained, and comparing the amplified signal thus obtained with a threshold noise level, within the same range of frequencies, which is characteristic of intact modules, this comparison making it possible to detect whether or not the module is intact.

The subject of the invention is also a device for implementing the process specified above, this device being characterized in that it comprises:

a hydrophone mounted on the low purge of each module, in contact with the permeate in such a way as to continuously listen to the noise of the liquid passing in filtration mode;

an amplifier of the signals delivered by the said sensor, and a comparator-analyser ensuring the comparison of the amplified noise signal from the sensor with a threshold noise level characteristic of an intact module, the analysis of the comparison making it possible to detect the possible presence of a leak on the said module.

Other characteristics and advantages of the present invention will emerge from the description below given with reference to the appended drawing in which:

FIG. 1 is a curve illustrating the acoustic signature of a module, and

FIG. 2 is a schematic representation illustrating an embodiment of the device according to the invention.

As will be understood, the process subject of the present invention relies on the detection of noise caused by the passage of treated fluid directly from the dirty side of the membrane (concentrate) to the clean side (permeate) through a filtration module fibre which is completely or partially broken.

BRIEF DESCRIPTION OF THE FIGURES

The present invention is not limited to the use of a microcomputer to analyse the signals. It is possible to collect the signals on the plant and analyse them on a central programmable process control unit.

DETAILED DESCRIPTION OF THE FIGURES

Figure 1:
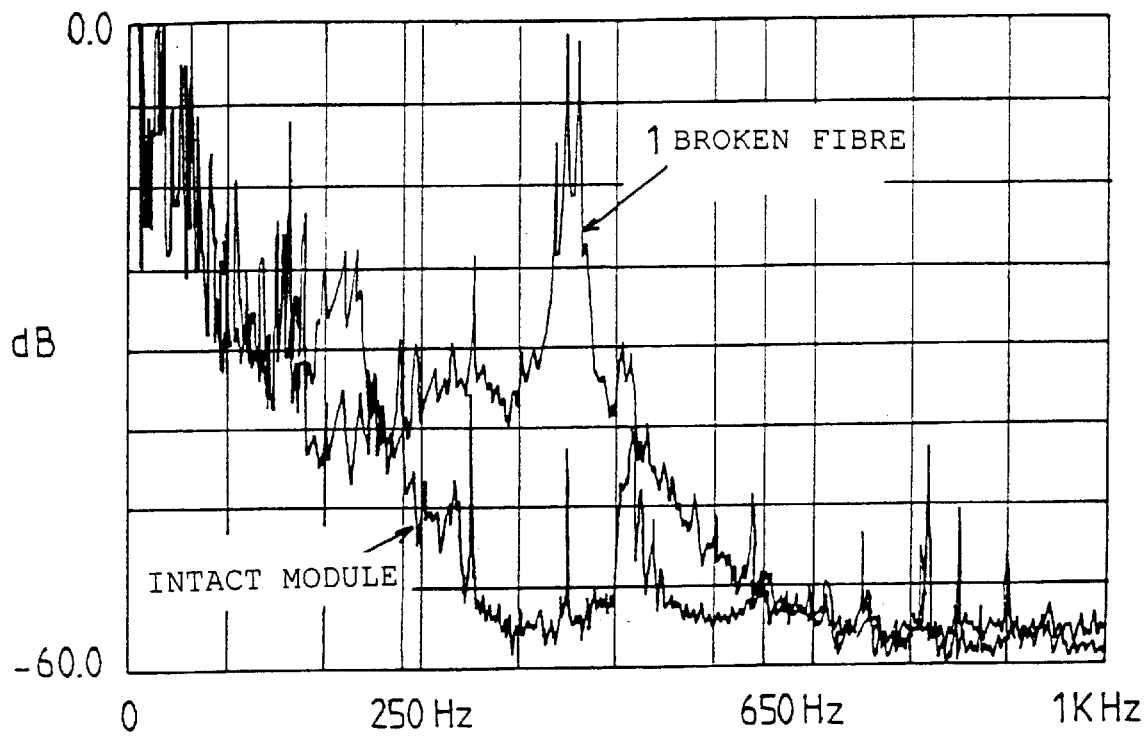
Figure 2:
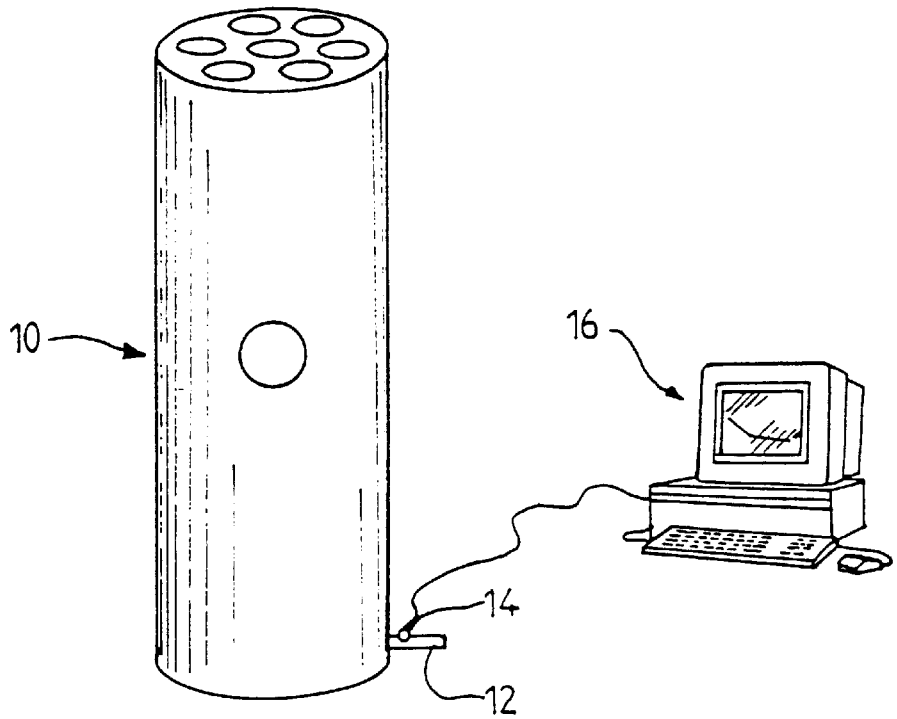

Reference number 10 in FIG. 2 shows a filtration module of the type comprising a number of hollow fibres grouped together in bundles. According to the invention, a sensor 14, in the form of a hydrophone, has been implanted on the low purge 12 of this module 10, making it possible to listen directly, in contact with the clean water (permeate), to the noise of the fluid passing. Each module such as 10 is provided with a hydrophone such as 14.

The signal delivered by the hydrophone is amplified and analysed by an electronic device in the form of a microcomputer 16 in order to measure the noise level, within a pre-selected frequency range, characteristic of intact modules. The result of the measurement is then compared with a threshold noise level, within the same frequency range, and this comparison makes it possible to indicate whether or not the module is intact.

The curve in FIG. 2 clearly shows how the presence of a broken fibre in the filtration module manifests itself, the characteristic increase in the noise level of the acoustic signature of the module making it possible to detect immediately an anomaly in the integrity of the said module.

Tests carried out by the present applicant have shown that the reference noise level for intact modules was homogeneous and did not vary appreciably from one site to another, nor from one position in the filtration machine to another position. It has thus been demonstrated that the concept of "acoustic signature", module by module, position by position or site by site, is not determining and that the recording of the initial noise level is not needed for detection.

It is possible according to the invention to envisage various uses among which the following can especially be cited.

implementation in filtration mode, without production shutdown, by listening to the noise caused by the passage of water through a possible leak;

It is understood, from reading the preceding description, that the process subject of the invention makes it possible, in filtration mode, to achieve almost continuous monitoring of the integrity of the modules, given that in a few seconds, automatically and at each filtration cycle, or at almost any time, it is possible to verify module by module, the integrity of the fibres of these modules. The indication of non-integrity makes it possible to identify a failing module. This result cannot be achieved in any circumstances by implementing the various processes which are currently known and mentioned above, and which involve a production shutdown to carry out the detection and the implementation of the different techniques for the identification of the defective module, after detection of a leak from the set of modules in the filtration machine, while the invention makes it possible to identify immediately the non-intact module.

It is of course understood that the present invention is not limited to the methods of implementation described and/or mentioned above but that it encompasses all variants.

What is claimed is:

1. Process for monitoring the integrity of hollow fiber filtration modules and for detecting leaks of treated liquid through a fiber completely or partially broken, in filtration mode, without production shutdown, comprising the steps of:

continuously detecting the noise caused by the passage of the liquid through a ruptured fiber;

amplifying the noise signal thus obtained; and comparing the amplified signal thus obtained with a threshold noise level within a range of frequencies which is characteristic of intact modules, this comparison making it possible to detect whether or not the module is intact.

2. A system for monitoring the integrity of hollow fiber filtration modules comprising:

hydrophone means mounted on the drain of each module in contact with clean liquid or permeate flowing there through for continuously monitoring noise of the flowing liquid in filtration mode;

an amplifier for amplifying signals delivered by the said hydrophone means; and comparator-analyzer means for comparing the amplified noise signal from the hydrophone with a noise level exceeding a threshold level, within a range of frequencies which is characteristic of an intact module, analysis of the comparison making it possible to detect a leak in said module.

* * * * *